United States Patent
Rostene et al.

(10) Patent No.: US 9,095,591 B2
(45) Date of Patent: Aug. 4, 2015

(54) PHARMACEUTICAL COMPOSITION FOR USE IN THE TREATMENT OF GLAUCOMA

(75) Inventors: William Rostene, Paris (FR); Alexandre Denoyer, Paris (FR); Christophe Baudouin, Paris (FR); David Godefroy, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 283 days.

(21) Appl. No.: 13/807,355

(22) PCT Filed: Jun. 24, 2011

(86) PCT No.: PCT/EP2011/060638
§ 371 (c)(1),
(2), (4) Date: Mar. 19, 2013

(87) PCT Pub. No.: WO2012/000904
PCT Pub. Date: Jan. 5, 2012

(65) Prior Publication Data
US 2013/0172370 A1    Jul. 4, 2013

(30) Foreign Application Priority Data
Jun. 28, 2010    (EP) .................................. 10305693

(51) Int. Cl.
A01N 43/90    (2006.01)
A61K 31/519    (2006.01)

(52) U.S. Cl.
CPC .................................. *A61K 31/519* (2013.01)

(58) Field of Classification Search
None
See application file for complete search history.

(56) References Cited

U.S. PATENT DOCUMENTS

2009/0131312 A1*  5/2009  Blatt et al. ....................... 514/12
2010/0203103 A1*  8/2010  Dana et al. ..................... 424/429

FOREIGN PATENT DOCUMENTS

WO    2005/035534 A1    4/2005
WO    2009/025763 A2    2/2009

OTHER PUBLICATIONS

Jopling et al., Analysis of the pharmacokinetic/pharmacodynamic relationship of a small molecule CXCR3 antagonist, NBI-74330, using a murine CXCR3 internalization assay, 2007, British Journal of Pharmacology, 152, 1260-1271.*
Tripathi et al., Drug-Induced Glaucomas: Mechanism and Management, 2003, Drug Safety, 26, 749-767.*
Database WPI, Week 200533, Thomson Scientific, London, GB, retrieved from web 2010.
Pease et al., "Chemokine receptor antagonists: part 2", Expert Opinion on Therapeutic Patents, Feb. 2009, pp. 199-221, vol. 19, No. 2.
Liu et al., "Optimization of a series of quinazolinone-derived antagonists of CXCR3", Bioorganic & Medicinal Chemistry Letters, Jul. 10, 2009, pp. 5114-5118, vol. 19, Elsevier.
Jopling et al., "Analysis of the pharmacokinetic/pharmacodynamic relationship of a small molecule CXCR3 antagonist, NBI-74330, using a murine CXCR3 internalization assay", British Journal of Pharmacology, Nov. 5, 2007, pp. 1260-1271, vol. 152, Nature Publishing Group.
Rosenblum et al., "CXCR3 Antagonism Impairs the Development of Donor-reactive, IFN-Gamma-producing Effectors and Prolongs Allograft Survival", Transplantation, Feb. 15, 2009, pp. 360-369, vol. 87, No. 3.

* cited by examiner

*Primary Examiner* — Anna Pagonakis
*Assistant Examiner* — Daniel M Podgorski
(74) *Attorney, Agent, or Firm* — Whitham, Curtis, Christofferson & Cook, P.C.

(57) ABSTRACT

The present invention relates to a compound which is an antagonist of CXCR3 or an inhibitor of the CXCR3 receptor expression for the treatment of glaucoma.

6 Claims, 4 Drawing Sheets

PHARMACEUTICAL COMPOSITION FOR USE IN THE TREATMENT OF GLAUCOMA

FIELD OF THE INVENTION

Figure 1:
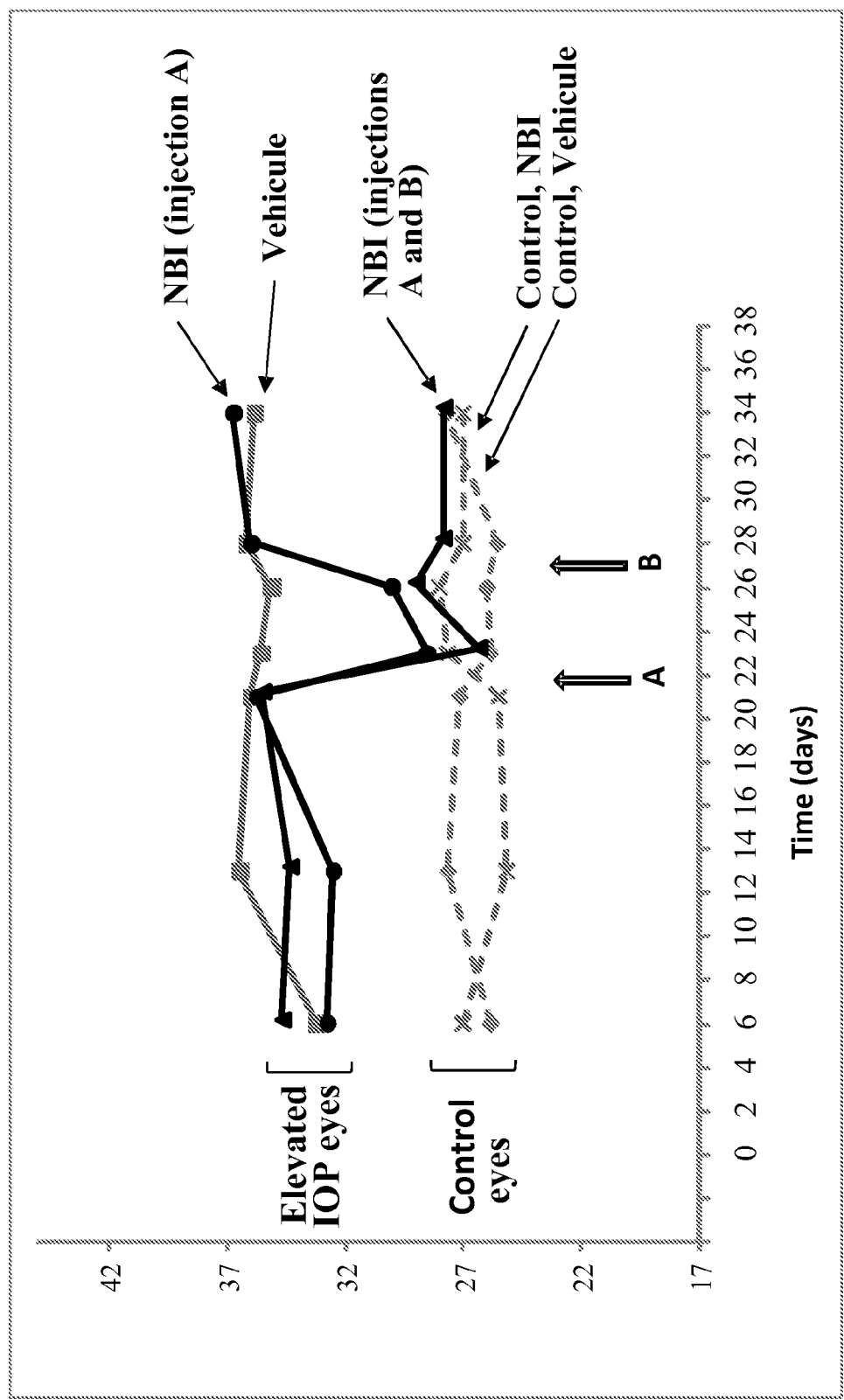

The invention relates to a compound which is an antagonist of CXCR3 or an inhibitor of the CXCR3 receptor expression for use in the treatment of glaucoma.

BACKGROUND OF THE INVENTION

Glaucoma is one of the most frequent ocular diseases which prevalence averages about 2% which is increasing with the aging of the population. Despite the wide advances in the medical and surgical managements of glaucoma, it still leads to clinical blindness in 1% to 30% of the patients, depending on the racial group and the country. So, there is a permanent need in the art for new molecules for the treatment of glaucoma (see for example Cedrone C. et Al., 2008).

SUMMARY OF THE INVENTION

Trabecular meshwork (TM) is a functional and anatomic ocular entity located at the angle formed by the cornea and iris, which primary function is to control the intraocular pressure (IOP) by regulating the aqueous humor (AH) outflow. Abnormal increase in the trabecular outflow resistance leads to elevated IOP which is the most critical risk factor for glaucoma (see for example Sommer A., 1989) Hence, abnormally elevated IOP during both angle-closure or primary open-angle glaucoma is linked with glaucomatous neuroretinal degeneration causing visual impairments to blindness.

Surprisingly, the inventors discovered that the inhibition of CXCR3, induces a significant decrease in IOP and thereby may lead to the treatment of glaucoma.

Thus, a first object of the invention relates to a compound which is an antagonist of CXCR3 or an inhibitor of the CXCR3 receptor expression for use in the treatment of glaucoma.

Another object of the invention relates to a pharmaceutical composition for the treatment of glaucoma comprising a compound according to the invention and a pharmaceutically acceptable carrier.

DETAILED DESCRIPTION OF THE INVENTION

CXCR3 is well known. CXCR3 is a G.alpha.i protein-coupled receptor in the CXC chemokine receptor family. Other names for CXCR3 are G protein-coupled receptor 9 (GPR9) and CD183. There are two variants of CXCR3: CXCR3-A binds to the CXC chemokines CXCL9 (MIG), CXCL 10 (IP-10), and CXCL 11 (I-TAC) whereas CXCR3-B can also bind to CXCL4 in addition to CXCL9, CXCL10, and CXCL11. CXCR3 is able to regulate leukocyte trafficking. Binding of chemokines to CXCR3induces various cellular responses, most notably integrin activation, cytoskeletal changes and chemotactic migration. CXCR3-ligand interaction attracts Th1 cells and promotes Th1 cell maturation. As explained in the article Pease et al, (Pease et al., 2009, Expert Opin. Ther. Patents, 19(1):39-58) there is evidence for a role of CXCR3 in the pathophysiology of autoimmune diseases like psoriasis, transplant rejection and T-cell trafficking to sites of inflammation.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

Glaucoma may be divided in primary and secondary glaucoma.

Primary glaucoma may be divided in "open angle" and "angle-closure" glaucoma. Apart from both these main kinds of glaucoma, other pathologies can lead to an elevation of IOP, namely secondary glaucomas including post-uveitic glaucoma and steroid-induced glaucoma. So the compound according to the invention may be used to primary or secondary glaucoma.

A first object of the invention relates to a compound which is an antagonist of CXCR3 or an inhibitor of the CXCR3 receptor expression for use in the treatment of glaucoma.

In a preferred embodiment, said compound according to the invention is a CXCR3 antagonist.

In one embodiment, said CXCR3 antagonist may be a low molecular weight antagonist, e.g. a small organic molecule (natural or not).

The term "small organic molecule" refers to a molecule (natural or not) of a size comparable to those organic molecules generally used in pharmaceuticals. The term excludes biological macromolecules (e.g., proteins, nucleic acids, etc.). Preferred small organic molecules range in size up to about 10000 Da, more preferably up to 5000 Da, more preferably up to 2000 Da and most preferably up to about 1000 Da.

In one embodiment, the antagonist may bind to CXCR3 and block the binding of another compound on CXCR3.

In a particular embodiment, the compound according to the invention is NBI74330 (see for example Jopling L A et Al., 2007), AMG487 (see for example Jiwen Liu, et al., 2009, An-Rong Lia et al., 2008 or Johnson M. et al., 2007), AMG1237845 (see for example Rosenblum J M et al., 2009).

Antagonists of CXCR3 are well known in the state of the art (see for example, Pease J. E. el al, 2009, Expert Opin. Ther. Patents).

In a particular embodiment, the compound according to the invention may be a dihydro-quinazoline analog (see for example Pease J. E. et al, 2009, Expert Opin. Ther. or Liu J et al., 2009) like AMG487 (see for example Jiwen Liu, et al., 2009, An-Rong Lia et al., 2008 or Johnson M. et al., 2007).

In a particular embodiment, the compound according to the invention may be a piperidinyl-urea derivative (see for example Pease J. E. et al, 2009, Expert Opin. Ther.) like a 1-aryl-3-piperidin-4-yl-urea derivative (see for example Allen et Al., 2007) or a 5-(piperidin-4-yl)amino-1,2,4-thiadiazole derivative (see for example Watson et Al., 2007), or a tropenyl derivative (see for example Watson et Al., 2008) or a 2-aminoquinoline substituted piperidines derivative (see for example Knight et Al., 2008).

In a particular embodiment, the compound according to the invention may be a 4-aryl-[1,4] diazepine ethyl ureas derivative (see for example Pease J. E. et al, 2009, Expert Opin. Ther. and Cole A G, et al., 2006).

In a particular embodiment, the compound according to the invention may be a benzimidazole derivative or a 2-iminobenzimidazole (see for example Pease J. E. et al, 2009, Expert Opin. Ther., Hayes M E, Wallace G A, et Al., 2008 and Hayes M E, Breinlinger E C et Al., 2008).

In a particular embodiment, the compound according to the invention may be a benzetimide derivative (see for example Pease J. E. et al, 2009, Expert Opin. Ther. and Bongartz J P et al., 2008).

In another particular embodiment, the compound according to the invention may be an ergoline derivative (see for example Thoma G. et Al., 2009 or Choudhary M S et Al., 1995 and patent application WO2006128658).

In another particular embodiment, the compound according to the invention may be a heterocyclic substituted piperazine derivative (see for example patent applications WO2006088837 and WO2008008453).

In another particular embodiment, the compound according to the invention may be a heterocyclic substituted pyridine derivative (see for example patent applications WO2007109238 and WO2006088840).

In another particular embodiment, the compound according to the invention may be a imidazolium derivative (see for example Verzijl D. Et al., and patent application WO03101970).

In another particular embodiment, the compound according to the invention may be an imidazole derivative (see for example Du X. et Al, 2008).

In another particular embodiment, the compound according to the invention may be a piperazinyl-piperidine derivative (see for example McGuinness B F et Al., 2009).

In another particular embodiment, the compound according to the invention may be a Camphor sulfonamide derivative (see for example Wang Y et Al., 2009).

In another particular embodiment, the compound according to the invention may be a pyrazinyl substituted piperazine-piperidine derivative (see for example patent application WO2006088921).

In another particular embodiment, the compound according to the invention may be a pyridyl and phenyl substituted piperazine-piperidine derivative (see for example patent application WO2006088919).

In another particular embodiment, the compound according to the invention may be a piperazine-piperidine derivative (see for example patent application WO2006088836).

In another particular embodiment, the compound according to the invention may be a heteroaryl substituted pyrazinyl-piperazine-piperidine derivative (see for example patent application WO2006091428).

In another particular embodiment, the compound according to the invention may be an amine-linked pyridyl and phenyl substituted piperazine-piperidine derivative (see for example patent application WO2006088920).

In another particular embodiment, the compound according to the invention may be a thiazole derivative (see for example patent application WO2007064553).

In another particular embodiment, the compound according to the invention may be a substituted heterocyclic derivative (see for example patent application WO2007047202).

In another embodiment, the compound according to the invention me be a compound described in Crosignani et al 2010.

In another embodiment, CXCR3 antagonist of the invention may be an anti-CXCR3 antibody which neutralizes CXCR3 or an anti-CXCR3 fragment thereof which neutralizes CXCR3 (see for example Xie J H et Al., 2003).

Antibodies directed against CXCR3 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against CXCR3 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-CXCR3 single chain antibodies. CXCR3 antagonists useful in practicing the present invention also include anti-CXCR3 antibody fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed to allow rapid identification of fragments having the desired specificity to CXCR3.

Humanized anti-CXCR3 antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of CXCR3 are selected.

In still another embodiment, CXCR3 antagonists may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then, for this invention, neutralizing aptamers of CXCR3 are selected.

In a preferred embodiment, the compound according to the invention is an inhibitor of the CXCR3 receptor expression.

Small inhibitory RNAs (siRNAs) can also function as inhibitors of CXCR3 receptor gene expression for use in the present invention. CXCR3 receptor gene expression can be reduced by contacting a subject or cell with a small double stranded RNA (dsRNA), or a vector or construct causing the production of a small double stranded RNA, such that CXCR3 receptor gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of CXCR3 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of CXCR3 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of CXCR3 receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing CXCR3 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA.

Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes For example, a specific expression in Muller glial cells may be obtained through the promoter of the glutamine synthetase gene is suitable. The promoter can also be, e.g., a viral promoter, such as CMV promoter or any synthetic promoters.

In order to test the functionality of putative CXCR3 blocking compounds on intraocular pressure (IOP), an in vivo test is necessary. For that purpose a model of local eye hypertonia is highly relevant. The model of ocular hypertonia in rats by episcleral vein occlusion (Garcia-Valenzuela et al., 1995) as described in the figures can be used to test such molecules.

Another object of the invention relates to a method for treating glaucoma comprising administering to a subject in need thereof a therapeutically effective amount of compound which is an antagonist of CXCR3 or an inhibitor of the CXCR3 receptor expression as described above.

In one aspect, the invention relates to a method for treating glaucoma comprising administering to a subject in need thereof a therapeutically effective amount of a CXCR3 antagonist as above described.

Compounds of the invention may be administered in the form of a pharmaceutical composition, as defined below.

Preferably, said compound which is an antagonist of CXCR3 or an inhibitor of the CXCR3 receptor expression.

By a "therapeutically effective amount" is meant a sufficient amount of compound to treat and/or to prevent glaucoma disorder.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Compounds according to the invention may be used for the preparation of a pharmaceutical composition for the treatment of a glaucoma disorder.

Hence, the present invention also provides a pharmaceutical composition comprising an effective dose of an antagonist of CXCR3 or an inhibitor of the CXCR3 receptor expression, preferably a CXCR3 antagonist, according to the invention.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, parenteral, intraocular, intravenous, intramuscular or subcutaneous administration and the like.

Preferably, compositions of the inventions may be formulated for intraocular either with eye drops, subconjunctival or intravitreal administration.

More preferably, local ocular routes should be used such as intravitreous, topical, periocular injections (sub conjunctival, peri bulbar, latero bulbar, retro bulbar, sub tenon, supra choroidal), intra or peri ocular implants (intra sceral, peri scleral, episcleral), intra virteous implants, ocular surface implants or any releasing systems such as emulsions, solid non biodegradable or degradable implants or tablets, mini pumps or any topical formulations.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration; time release capsules; and any other form currently can be used.

Active ingredient may be also delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an active ingredient may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the active ingredient in a physiologically acceptable isotonic aqueous buffer. Further, the solution may include an acceptable surfactant to assist in dissolving the active ingredient. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the active ingredient is combined with a preservative in an appropriate vehicle, such as mineral oil, liquid lanolin, or white petrolatum. Sterile ophthalmic gel formulations may be prepared by suspending the active ingredient in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the active ingredient is less penetrating in the eye.

The invention will be further illustrated by the following figure and example. However, the example and figure should not be interpreted in any way as limiting the scope of the present invention.

FIGURE

FIG. 1: In Vivo Effect of the CXCR3 Inhibitor NBI74330 on the Intraocular Pressure (IOP) in a Rat Model of Surgically-Induced Glaucoma.

Subconjunctival injections of NBI74330 (1 µM) or vehicle were performed in glaucoma eyes and in control eyes. One single injection of NBI (A) induced a reduction in IOP during 3 days (p<0.001). Two injections of NBI (A and B) induced a decrease in IOP during 12 days (p<0.001). NBI or vehicle injections in control eyes did not influence the IOP. (In vivo measurements of the IOP using TonoPen).

Figure 2:
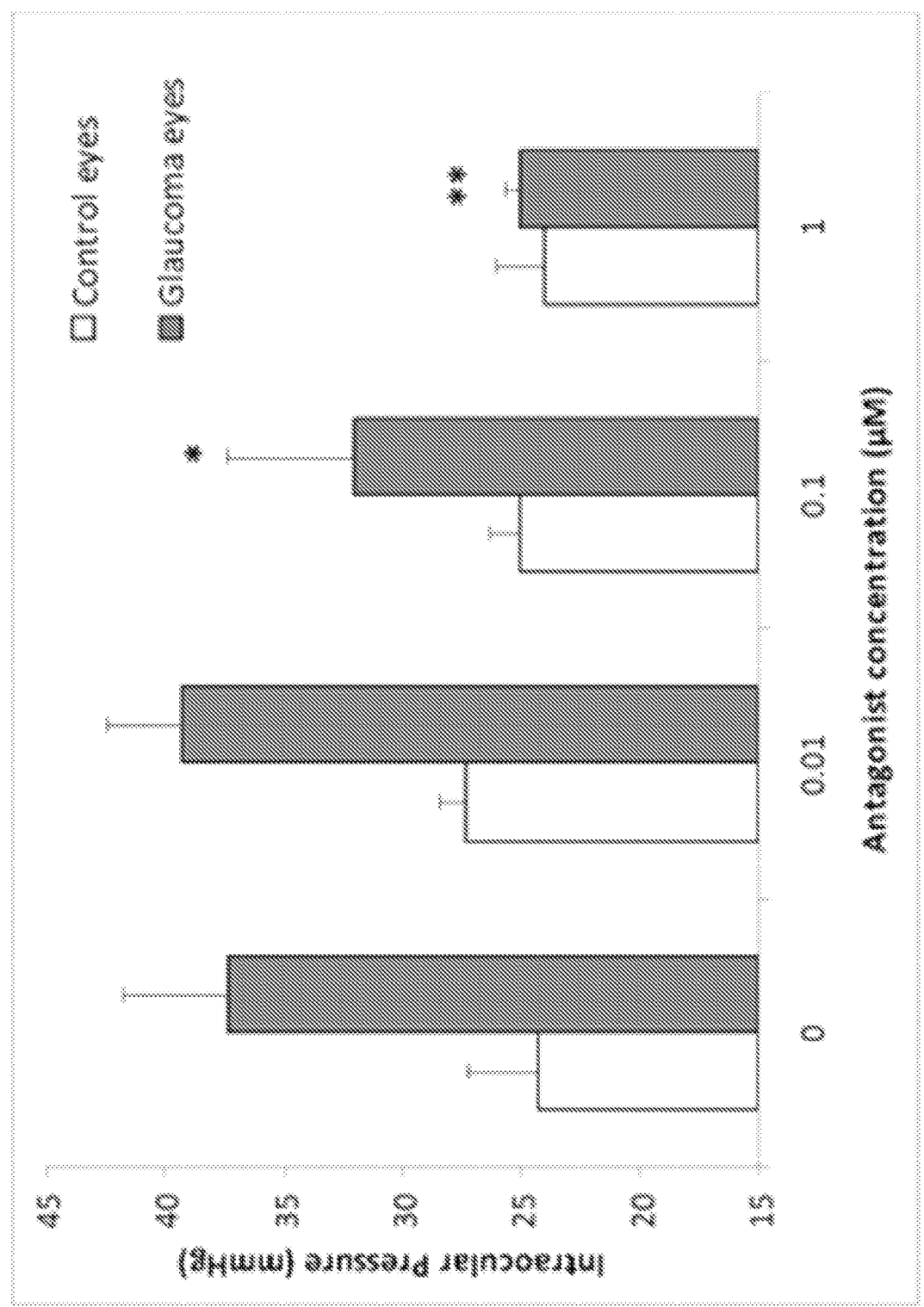

FIG. 2: Effect of CXCR3 Inhibitor NBI74330 on the Intraocular Pressure (IOP) in Function of the Dose.

NBI-74330 reduced the IOP in glaucomatous eyes (n=20) in a dose-dependent manner. Mann-Whitney U-test: *, P<0.05 and **, P<0.01 relative to vehicle-treated eyes.

Figure 3:
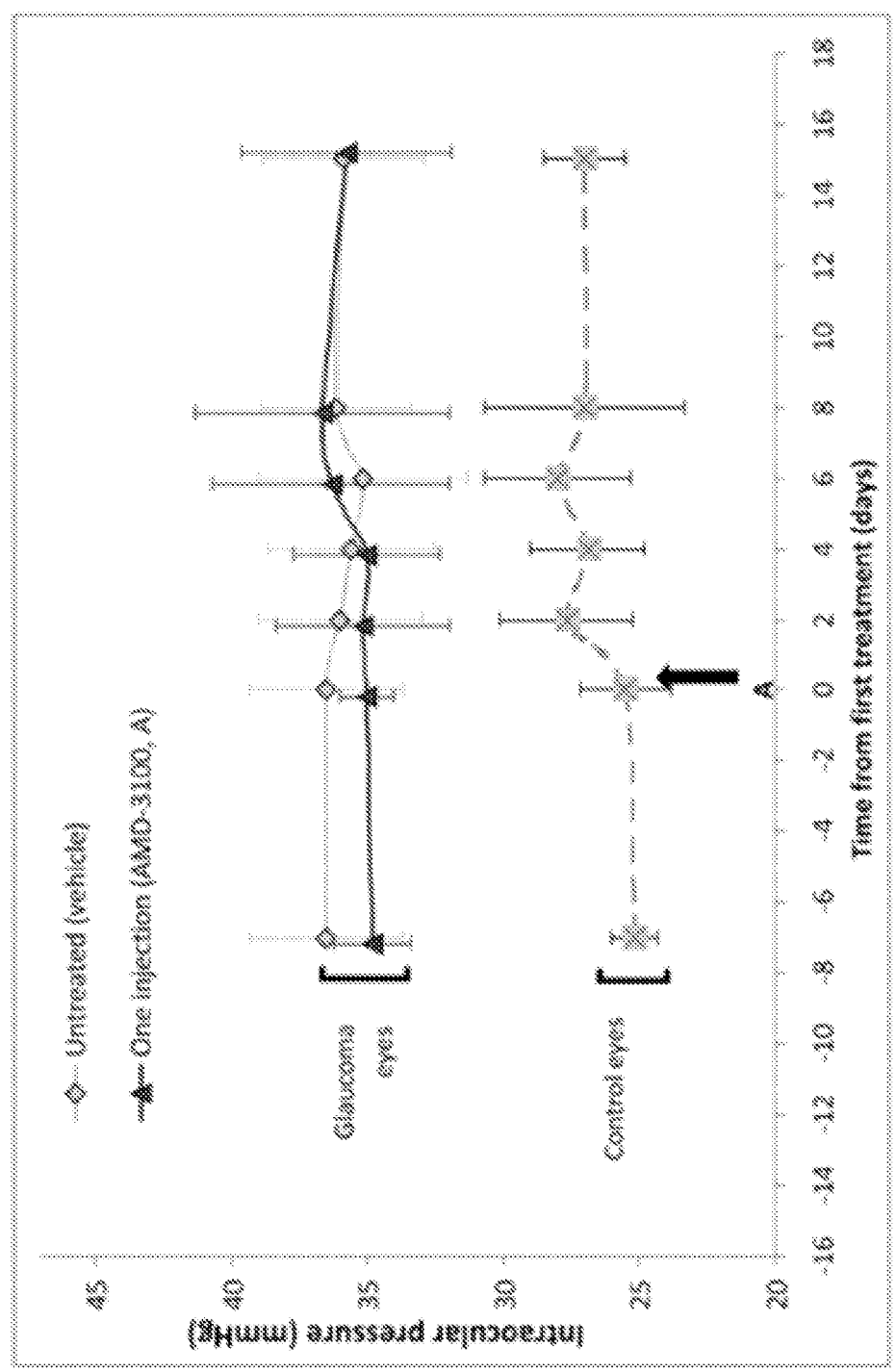

FIG. 3: Selective CXCR4 Antagonist has No Effect in IOP.

AMD3100 did not affect the IOP in glaucomatous eyes or in nonglaucomatous controls (n=20).

Figure 4:
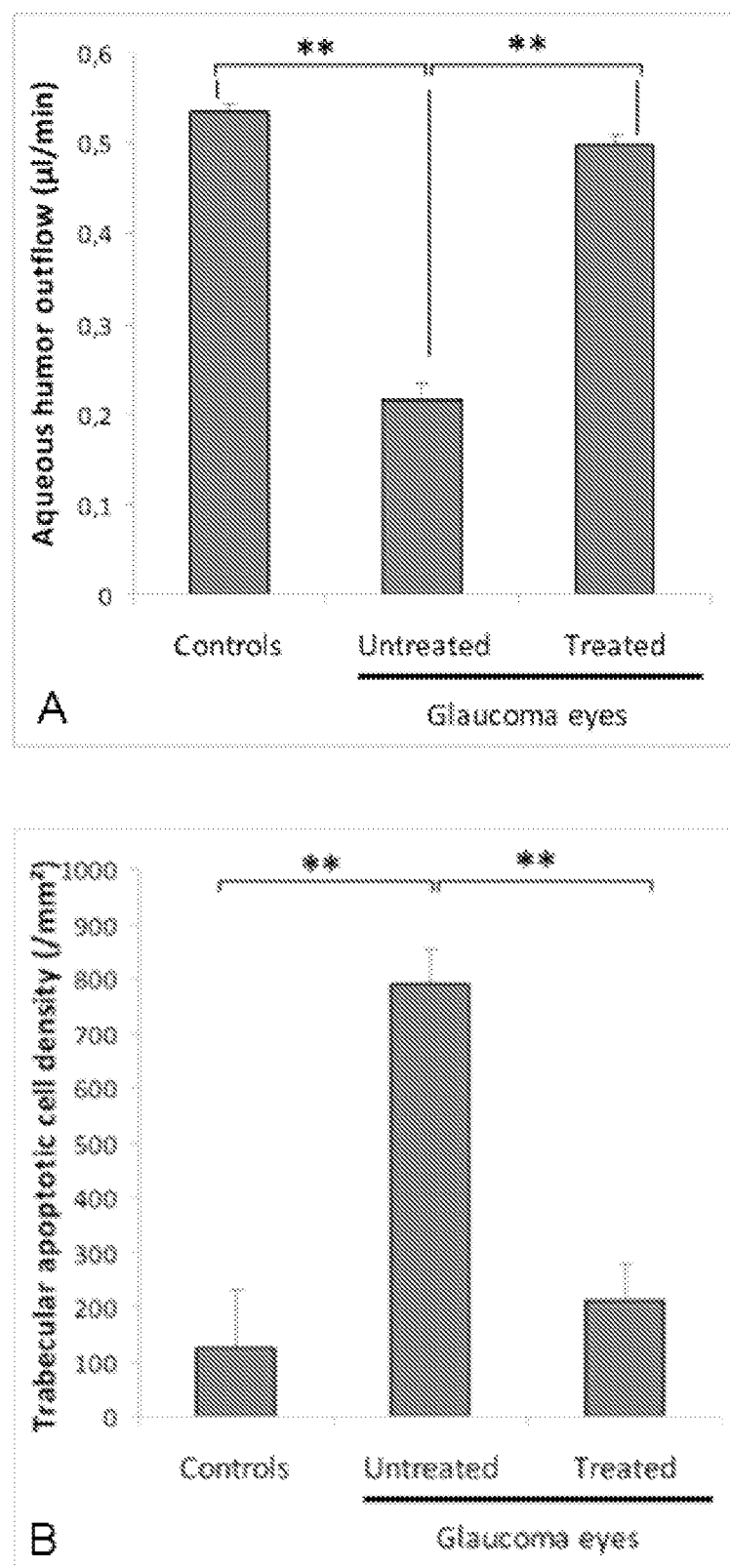

FIG. 4: In Vivo Treatment with a CXCR3 Antagonist Increased Aqueous Humor Outflow and Trabecular Filtration, and Decreased Trabecular Cell Apoptosis in an Animal Model of Glaucoma.

Aqueous humor outflow (AHO), trabecular percent effective filtration length (PEFL), and trabecular cell apoptosis were evaluated in normal eyes (n=20) and in glaucomatous eyes (n=20) treated with or without NBI-74330 (1 µM, 100 µL, two subconjunctival injections). (a) AHO was improved in NBI-74330-treated glaucomatous eyes (n=20) compared to vehicle-treated glaucomatous eyes. (b) NBI-74330 treatment significantly reduced the amount of apoptotic TCs in glaucomatous eyes.

EXAMPLE

Material & Methods

Animal Model and In Vivo Experiments.

Male 8-week-old Brown Norway rats weighing 300-400 g were housed in Jussieu animal house (UMRS968, Vision Institute, Paris, France). All experiments were conducted in accordance with the Association for Research in Vision and Ophthalmology for the Use of Animals in Ophthalmic research. Ocular integrity was checked using slit lamp biomicroscope. Surgical model of elevated IOP was induced in the right eye of each rat by cauterization of three episcleral veins after conjunctival dissection as previously reported [Bayer A U et Al., 2001 and Garcia-Valenzuela E et Al., 1995] under general anaesthesia (intra peritoneal injection of ketamine 75 mg/kg and xylazine 10 mg/kg). Left eyes underwent conjunctival dissection only as controls. After the surgery, animals were maintained for a 1-month period and monitored for IOP three times a week using a handheld tonometer (Tonopen, Medtronics, Jacksonville, Fla.) without sedation. 30 animals presenting a stable elevated IOP were included and randomly divided in three equal groups: in both eyes, 10 rats received one subconjunctival injection of NBI74330 (1 µM, 100 µl), 10 rats received one injection of NBI74330 followed by a second one five days after, and 10 rats received a vehicle injection (PBS, 100 µl). IOP was monitored every two days by one independent person i.e. who was blind of the treatment. At the end of the experiments, animals were euthanized and the eyes were immediately conditioned for IHC.

Results

Treatment with a CXCR3 Antagonist Lowers the Intra Ocular Pressure and Reduces TM Cell Apoptosis in a Rat Model of Glaucoma.

Subconjunctival injection of NBI74330 (1 µM, 100 µl) induced an IOP lowering in an animal eye model of surgically-induced elevated IOP (FIG. 1). In the group undergoing a single injection, this effect was significant the 2nd to the 5th day after the treatment, reaching the average IOP level of control eyes. When a second injection was performed 4 days after the first one, a significantly low IOP was maintained until the end of the experiments. In non-operated control eyes, NBI74330, AMD3100 or PBS had no effect on the basal IOP level.

Eyes were conditioned into cryosections and assessed for apoptosis using TUNEL-labeling. TM was identified in each cryosections as a pigmented slim tissue on the posterior sclera-cornea beside the iris root and just above the endothelial Schlemm's canals. Apoptosis was higher in trabecular cells of untreated glaucoma eyes than in glaucoma eyes treated with NBI74330. Moreover, endothelial Schlemm cells and retinal cells—especially in the inner nuclear layer and ganglion cell layer—presented more TUNEL labeling in the untreated glaucoma eyes than in glaucoma eyes treated with NBI74330.

Moreover, NBI-74330 reduced IOP in a dose-dependent manner (FIG. 2). In contrast to blockade of CXCR3, subconjunctival injections of a CXCR4 selective antagonist, AMD-3100, did not influence IOP in glaucomatous eyes (FIG. 3). In nonglaucomatous control eyes, neither NBI-74330 nor AMD-3100 (inhibitor of CXCR4) had any effect on IOP.

Thus, selective CXCR3 antagonist reduces IOP in a rat model of glaucoma, whereas selective CXCR4 antagonist has no effect.

We can conclude that selective antagonist of CXCR3 and selective inhibitor of the CXCR3 receptor expression may be used for the treatment of glaucoma.

In Vivo Treatment with Selective CXCR3 Antagonist Restores the Trabecular Filtrating Function by Protecting Trabecular Cells from Death.

Investigations were conducted in order to study mechanisms involved in the NBI-74330-related decrease in IOP. Aqueous humor outflow was measured by in vivo fluorophotometry (FIG. 4A) and the trabecular aqueous outflow evaluated by fluorescent microsphere injection and ex vivo confocal imaging of TMs (data not shown). Interestingly, we observed a decrease in aqueous humor outflow along with a decrease in the TM filtrating surface in hypertensive eyes compared to controls 1 month after the surgical procedure. This decrease in trabecular outflow facility is similar to what is observed during hypertensive POAG in humans. In our model, aqueous humor outflow impairment was significantly reversed in NBI-74330-treated eyes compared to vehicle-treated controls. Moreover, the trabecular filtrating surface, namely percent effective filtration length (PEFL), was also significantly improved by NBI-74330 treatment. In parallel, rat TM tissues were assessed for cellularity and apoptosis by immunohistofluorescence and TUNEL-labeling.

In our model, TC apoptosis was significantly increased in glaucoma eyes compared to normotensive control eyes (FIG. 4B). Trabecular apoptosis was reversed in glaucoma eyes treated with NBI-74330 compared to untreated glaucoma eyes. No inflammatory cell infiltration was found in the TM of glaucoma eyes throughout the experimental period, as revealed by a lack of either anti-CD45 or anti-CD11b reactive cells. Moreover, NBI-related reduction in IOP was associated with a decrease in retinal ganglion cell apoptosis as assessed by TUNEL-labeling (4.01±0.86, 11.11±3.62, and 5.73±1.15 apoptotic retinal ganglion cells/mm for control eyes, untreated glaucomatous eyes, and NBI-treated glaucomatous eyes, respectively; $P<0.05$ between each group). These data together suggest that blocking CXCR3 may lower experimentally induced ocular hypertension and protect retinal ganglion cells from apoptosis by restoring the TM filtrating function.

References

Allen D R, Bolt A, Chapman G A, et al. Identification and structure-activity relationships of 1-aryl-3-piperidin-4-yl-urea derivatives as CXCR3 receptor antagonists. Bioorg Med Chem Lett 2007; 17:697-701.

An-Rong Lia, Michael G. Johnsona, Jiwen Liva, Xiaoqi Chena, Xiaohui Dua, Jeffrey T. Mihalica, Jeffrey Deignana, Darin J. Gustina, Jason Duquettea, Zice Fua, Liusheng Zhua, Andrew P. Marcusa, Phillipe Bergerona, Lawrence R. McGeea, Jay Danaoa, Bryan Lemona, Teresa Carabeoa, Timothy Sullivana, Ji Maa, Liang Tanga, George Tonna, Tassie L. Collinsa and Julio C. Medina. Optimization of the heterocyclic core of the quinazolinone-derived CXCR3 antagonists. Bioorg Med Chem. Lett. 2008 Jan. 15; 18(2): 688-93.

Bayer A U, Danias J, Brodie S, Maag K P, Chen B, Shen F, Podos S M, Mittag T W. Electroretinographic abnormalities in a rat glaucoma model with chronic elevated intraocular pressure. Exp Eye Res. 2001; 72:667-77.

Bongartz J P, Buntinx M, Coesemans E, et al. Synthesis and structure-activity relationship of benzetimide derivatives as human CXCR3 antagonists. Bioorg Med Chem Lett 2008.

Cedrone C, Mancino R, Cerulli A, Cesareo M, Nucci C. Epidemiology of primary glaucoma: prevalence, incidence, and blinding effects. Prog Brain Res. 2008; 173:3-14.

Choudhary M S, Sachs N, Uluer A, et al. Differential ergoline and ergopeptine binding to 5-hydroxytryptamine-2A receptors: ergolines require an aromatic residue at position 340 for high affinity binding. Mol Pharmacol 1995; 47:450-7.

Cole A G, Stroke I L, Brescia M R, et al. Identification and initial evaluation of 4-N-aryl-[1,4]diazepane ureas as potent CXCR3 antagonists. Bioorg Med Chem Lett 2006; 16:200-3.

Crosignani Stefano, Marc Missotten, Christophe Cleva, Ruggero Dondi, Yann Ratinaud, Yves Humbert, Ashis Baran Mandal, Agnes Bombrun, Christine Power, André Chollet a, Amanda Proudfoot. Discovery of a novel series of CXCR3 antagonists. Bioorganic & Medicinal Chemistry Letters 20 (2010) 3614-3617.

Du X, Chen X, Mihalic J T, Deignan J, Duquette J, Li A R, Lemon B, Ma J, Miao S, Ebsworth K, Sullivan T J, Tonn G, Collins T L, Medina J C. Design and optimization of imidazole derivatives as potent CXCR3 antagonists. Bioorg Med Chem. Lett. 2008 Jan. 15; 18(2):608-13.

Garcia-Valenzuela E, Shareef S, Walsh J, Sharma S C. Programmed cell death of retinal ganglion cells during experimental glaucoma. Exp Eye Res. 1995; 61:33-44.

Gebhard Thoma, Rolf Baenteli, Ian Lewis, Trixie Wagner, Lukas Oberer, Wolfgang Blum, Fraser Glickman, Markus B. Streiff, Hans-Guenter Zerwes. Special ergolines are highly selective, potent antagonists of the chemokine receptor CXCR3: Discovery, characterization and preliminary SAR of a promising lead. Bioorganic & Medicinal Chemistry Letters 19 (2009) 6185-6188.

Hayes M E, Breinlinger E C, Wallace G A, et al. Lead identification of 2-iminobenzimidazole antagonists of the chemokine receptor CXCR3. Bioorg Med Chem Lett 2008; 18:2414-9.

Hayes M E, Wallace G A, Grongsaard P, et al. Discovery of small molecule benzimidazole antagonists of the chemokine receptor CXCR3. Bioorg Med Chem Lett 2008; 18:1573-6.

James E Pease & Richard Horuk. Chemokine receptor antagonists: part 2. Expert Opin. Ther. Patents (2009) 19(2): 199-221.

Jiwen Liu, Zice Fua, An-Rong Lia, Michael Johnsona, Liusheng Zhua, Andrew Marcusa, Jay Danaoa, Tim Sullivana, George Tonna, Tassie Collinsa and Julio Medinaa. Optimization of a series of quinazolinone-derived antagonists of CXCR3. Bioorg Med Chem. Lett. 2009 Sep. 1; 19(17):5114-8.

Jopling L A, Watt G F, Fisher S, Birch H, Coggon S, Christie M I. Analysis of the pharmacokinetic/pharmacodynamic relationship of a small molecule CXCR3 antagonist, NBI-74330, using a murine CXCR3 internalization assay. Br J. Pharmacol. 2007; 152:1260-71.

Johnson M, Li A R, Liu J, Fu Z, Zhu L, Miao S, Wang X, Xu Q, Huang A, Marcus A, Xu F, Ebsworth K, Sablan E, Danao J, Kumer J, Dairaghi D, Lawrence C, Sullivan T, Tonn G, Schall T, Collins T, Medina J. Discovery and optimization of a series of quinazolinone-derived antagonists of CXCR3. Bioorg Med Chem. Lett. 2007 Jun. 15; 17(12):3339-43.

Knight R L, Allen D R, Birch H L, et al. Development of CXCR3 antagonists. Part 4: discovery of 2-amino-(4-tropinyl)quinolines. Bioorg Med Chem Lett 2008; 18:629-33

James E Pease & Richard Horuk. Chemokine receptor antagonists: part 2. Expert Opin. Ther. Patents (2009) 19(2): 199-221.

Liu J, Fu Z, Li A R, Johnson M, Zhu L, Marcus A, Danao J, Sullivan T, Tonn G, Collins T, Medina J. Optimization of a series of quinazolinone-derived antagonists of CXCR3. Bioorg Med Chem. Lett. 2009 Sep. 1; 19(17):5114-8. Epub 2009 Jul. 10.

McGuinness B F, Carroll C D, Zawacki L G, Dong G, Yang C, Hobbs D W, Jacob-Samuel B, Hall J W 3rd, Jenh C H, Kozlowski J A, Anilkumar G N, Rosenblum S B. Novel CXCR3 antagonists with a piperazinyl-piperidine core. Bioorg Med Chem. Lett. 2009 Sep. 1; 19(17):5205-8. Epub 2009 Jul. 9.

Rosenblum J M, Zhang Q W, Siu G, Collins T L, Sullivan T, Dairaghi D J, Medina J C, Fairchild R L. CXCR3 antagonism impairs the development of donor-reactive, IFN-gamma-producing effectors and prolongs allograft survival. Transplantation. 2009 Feb. 15; 87(3):360-9.

Sommer A. Intraocular pressure and glaucoma. Am J. Ophthalmol. 1989; 107:186-8.

Sommer A. Intraocular pressure and glaucoma. Am J. Ophthalmol. 1989; 107:186-8.

Vergote D, Butler G S, Ooms M, Cox J H, Silva C, Hollenberg M D, Jhamandas J H, Overall C M, Power C. Proteolytic processing of SDF-1alpha reveals a change in receptor specificity mediating HIV-associated neurodegeneration. Proc Natl Acad Sci USA. 2006; 103:19182-7.

Verzijl D, Storelli S, Scholten D J, et al. Noncompetitive antagonism and inverse agonism as mechanism of action of nonpeptidergic antagonists at primate and rodent CXCR3 chemokine receptors. J Pharmacol Exp Ther 2008; 325:544-55.

Wang Y, Busch-Petersen J, Wang F, Kiesow T J, Graybill T L, Jin J, Yang Z, Foley J J, Hunsberger G E, Schmidt D B, Sarau H M, Capper-Spudich E A, Wu Z, Fisher L S, McQueney M S, Rivero R A, Widdowson K L. Camphor sulfonamide derivatives as novel, potent and selective CXCR3 antagonists. Bioorg Med Chem. Lett. 2009 Jan. 1; 19(1):114-8. Epub 2008 Nov. 6.

Watson R J, Allen D R, Birch H L, et al. Development of CXCR3 antagonists. Part 2: Identification of 2-amino(4-piperidinyl)azoles as potent CXCR3 antagonists. Bioorg Med Chem Lett 2007; 17:6806-10.

Watson R J, Allen D R, Birch H L, et al. Development of CXCR3 antagonists. Part 3: Tropenyl and homotropenyl-piperidine urea derivatives. Bioorg Med Chem Lett 2008; 18:147-51.

Xie J H, Nomura N, Lu M, et al. Antibody-mediated blockade of the CXCR3 chemokine receptor results in diminished recruitment of T helper 1 cells into sites of inflammation. J Leukoc Biol 2003; 73:771-80.

Throughout this application, various references describe the state of the art to which this invention pertains. The disclosures of these references are hereby incorporated by reference into the present disclosure.

The invention claimed is:

1. A method for treating glaucoma in a subject in need thereof, comprising administering to eye tissue of said subject a therapeutically effective amount of a compound which is an antagonist of CXCR3 or an inhibitor of CXCR3 receptor expression, wherein said compound is the sole active agent for treating glaucoma in said subject, and wherein said compound is
   (N-[1-[3-(4-ethoxyphenyl)-4-oxopyrido[2,3-d]pyrimidin-2-yl]ethyl]-2-[4-fluoro-3-(trifluoromethyl)phenyl]-N-(pyridin-3-ylmethyl)acetamide);
   (N-[(1R)-1[3-(4-ethoxyphenyl)-4-oxopyrido[2,3-d]pyridin-2-yl]ethyl]-N-(pyridin-3-ylmethyl)-2-[4-(trifluoromethoxy) phenyl]acetamide);

or

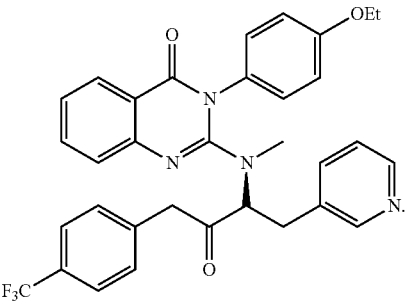

2. The method of claim 1, wherein said compound is a compound which inhibits the level of the CXCR3 protein on the cell surface.

3. The method of claim 1, wherein said glaucoma is an "open angle" or an "angle-closure" glaucoma.

4. The method of claim 1, wherein said administering step is selected from the group consisting of ocular, periocular, conjunctival, subtenon, intracameral, intravitral, intraocular, subretinal, subconjunctival, suprochoroidal, retrobulbar, intracanalicular and intranasal administration.

5. The method of claim 1, wherein said compound is in a solution that is administered directly to eye tissue by a means selected from the group consisting of eye drops, injection, emulsion, emulsion releasing system, minipump, and implanted minipump.

6. The method of claim 5, wherein said eye drops is an oil or aqueous solution suitable for administration to the ocular surface.

* * * * *